US010426592B2

(12) United States Patent
Folan et al.

(10) Patent No.: US 10,426,592 B2
(45) Date of Patent: Oct. 1, 2019

(54) IMPLANTABLE MEDICAL DEVICE WITH REDUCED MIGRATION CAPABILITIES

(71) Applicant: BOSTON SCIENTIFIC SCIMED, INC., Maple Grove, MN (US)

(72) Inventors: Martyn G. Folan, Galway (IE); Thomas M. Keating, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 9 days.

(21) Appl. No.: 15/483,561

(22) Filed: Apr. 10, 2017

(65) Prior Publication Data

US 2017/0290653 A1    Oct. 12, 2017

Related U.S. Application Data

(60) Provisional application No. 62/321,148, filed on Apr. 11, 2016.

(51) Int. Cl.
*A61F 2/04*    (2013.01)
*A61F 2/90*    (2013.01)
(Continued)

(52) U.S. Cl.
CPC ............... *A61F 2/04* (2013.01); *A61F 2/90* (2013.01); *A61F 2/07* (2013.01); *A61F 2002/9528* (2013.01); *A61F 2210/0076* (2013.01); *A61F 2220/0058* (2013.01); *A61F 2220/0075* (2013.01); *A61F 2230/0069* (2013.01); *A61F 2250/0023* (2013.01);
(Continued)

(58) Field of Classification Search
CPC ...... A61F 2/04; A61F 2/90; A61F 2/07; A61F 2002/9528; A61F 2210/0076; A61F 2220/0058; A61F 2220/0075; A61F 2230/0069; A61F 2250/0023; A61F 2250/0051; A61F 2250/0059; A61F 2250/0096
See application file for complete search history.

(56) References Cited

U.S. PATENT DOCUMENTS 5,035,706 A    7/1991    Giantureo et al.
5,238,004 A    8/1993    Sahatjian et al.
(Continued)

FOREIGN PATENT DOCUMENTS

| EP | 0481365 A1 | 4/1992 |
|---|---|---|
| WO | 0042949 A2 | 7/2000 |
| WO | 2006124541 A2 | 11/2006 |

*Primary Examiner* — Christopher D. Prone
*Assistant Examiner* — Tiffany P Shipmon
(74) *Attorney, Agent, or Firm* — Seager, Tufte & Wickhem, LLP

(57)    ABSTRACT

Medical devices and methods for making and using a medical device are disclosed. An example medical device may include a stent that comprises a first covered region formed of one or more interwoven filaments and a covering. The stent may also comprise a second uncovered region adjacent the first covered region. The second uncovered region may include a knitted filament. A first end of the knitted filament may be attached to the first covered region. The knitted filament is configured to be unraveled to remove both the first covered region and the second uncovered region of the stent while the first end of the knitted stent remains attached to the first covered region.

18 Claims, 13 Drawing Sheets

(51) Int. Cl.
 *A61F 2/07* (2013.01)
 *A61F 2/95* (2013.01)

(52) U.S. Cl.
 CPC ............... *A61F 2250/0051* (2013.01); *A61F 2250/0059* (2013.01); *A61F 2250/0096* (2013.01)

(56) References Cited

U.S. PATENT DOCUMENTS

| | | |
|---|---|---|
| 5,405,378 A | 4/1995 | Strecker |
| 5,514,176 A | 5/1996 | Bosley, Jr. |
| 5,662,713 A | 9/1997 | Andersen et al. |
| 6,083,257 A | 7/2000 | Taylor et al. |
| 6,221,099 B1 | 4/2001 | Andersen et al. |
| 6,355,070 B1 | 3/2002 | Andersen et al. |
| 6,485,515 B2 | 11/2002 | Strecker |
| 6,505,654 B1 | 1/2003 | Andersen et al. |
| 6,508,803 B1 | 1/2003 | Horikawa et al. |
| 6,821,291 B2 | 11/2004 | Bolea et al. |
| 7,547,321 B2 | 6/2009 | Silvestri et al. |
| 7,682,381 B2 | 3/2010 | Rakos et al. |
| 7,815,589 B2 | 10/2010 | Meade et al. |
| 7,875,068 B2 | 1/2011 | Mangiardi et al. |
| 8,057,420 B2 | 11/2011 | Meade et al. |
| 8,197,529 B2 | 6/2012 | Cully et al. |
| 8,398,699 B2 | 3/2013 | Shin et al. |
| 8,414,635 B2 | 4/2013 | Hyodoh et al. |
| 8,491,647 B2 | 7/2013 | Colgan et al. |
| 8,663,541 B2 | 3/2014 | Chun et al. |
| 8,696,736 B2 | 4/2014 | Yachia et al. |
| 8,739,382 B2 | 6/2014 | Sheldon et al. |
| 8,753,407 B2 | 6/2014 | Nguyen |
| 8,771,219 B2 | 7/2014 | Meade et al. |
| 2004/0176832 A1 | 9/2004 | Hartley et al. |
| 2007/0055364 A1 | 3/2007 | Hossainy et al. |
| 2011/0060398 A1* | 3/2011 | Tupil ............... A61F 2/07 623/1.15 |
| 2011/0087146 A1 | 4/2011 | Ryan et al. |
| 2011/0245851 A1 | 10/2011 | Ducharme et al. |
| 2012/0143306 A1 | 6/2012 | Cully et al. |
| 2012/0158122 A1* | 6/2012 | Mattson ............ A61F 2/856 623/1.15 |
| 2013/0018215 A1 | 1/2013 | Snider et al. |
| 2013/0245745 A1* | 9/2013 | Vong ............... A61F 2/885 623/1.12 |
| 2015/0282922 A1 | 10/2015 | Hingston et al. |
| 2015/0282960 A1 | 10/2015 | Harris |
| 2016/0206449 A1 | 7/2016 | Mort et al. |

* cited by examiner

IMPLANTABLE MEDICAL DEVICE WITH REDUCED MIGRATION CAPABILITIES

CROSS REFERENCE TO RELATED APPLICATIONS

This application claims the benefit of U.S. Provisional Patent Application Ser. No. 62/321,148 filed on Apr. 11, 2016, the disclosure of which is incorporated herein by reference.

TECHNICAL FIELD

The present disclosure pertains to medical devices, and methods for manufacturing and using medical devices. More particularly, the present disclosure pertains to elongated implantable medical devices with reduced migration capabilities.

BACKGROUND

A wide variety of intracorporeal medical devices have been developed for medical use, for example, intravascular use. In some instances medical devices (e.g., self-expanding stents) are placed in the esophagus for the treatment of esophageal strictures. However, over time a medical device positioned in the esophagus may shift its position away from its initial placement. For example, in some instances a self-expanding stent may migrate away from its preferred treatment position within the esophagus (e.g., due to peristaltic motion), and therefore, may need to be removed and/or repositioned. Hence, in some instances it may be desirable to design medical devices (e.g., self-expanding stents) that maintain a preferred placement within a body lumen (e.g., the esophagus) while also providing a means to remove the medical device from the body lumen (e.g., the esophagus) altogether. Examples are disclosed herein which allow for the anchoring of a medical device via tissue ingrowth, while also providing a means from removing the medical device from a body lumen. These devices are manufactured by any one of a variety of different manufacturing methods and may be used according to any one of a variety of methods.

SUMMARY

This disclosure provides design, material, manufacturing method, and use alternatives for medical devices. An example medical device may include a stent that comprises a first covered region formed of one or more interwoven filaments and a covering. The stent may also comprise a second uncovered region adjacent the first covered region. The second uncovered region may include a knitted filament. A first end of the knitted filament may be attached to the first covered region. The knitted filament is configured to be unraveled to remove both the first covered region and the second uncovered region of the stent while the first end of the knitted stent remains attached to the first covered region.

Alternatively or additionally to any of the embodiments above, wherein the one or more interwoven filaments of the first covered region include a plurality of braided filaments.

Alternatively or additionally to any of the embodiments above, wherein the one or more interwoven filaments of the first covered region include a knitted filament.

Alternatively or additionally to any of the embodiments above, wherein the knitted filament of the second uncovered region and the knitted filament of the first covered region comprise a single knitted filament.

Alternatively or additionally to any of the embodiments above, wherein the first end of the knitted filament is attached to the first covered region at a first attachment point.

Alternatively or additionally to any of the embodiments above, wherein the first weld point is configured to terminate the unraveling of the knitted filament beyond the first attachment point.

Alternatively or additionally to any of the embodiments above, wherein the knitted filament of the second region includes a second end, and wherein the second end is attached to an intermediate portion of the knitted filament at a second attachment point.

Alternatively or additionally to any of the embodiments above, wherein the second weld point is configured to separate from the intermediate portion of the knitted filament.

Alternatively or additionally to any of the embodiments above, wherein separating the attachment point from the intermediate portion of the knitted filament permits the unraveling of the second uncovered region of the stent.

Alternatively or additionally to any of the embodiments above, wherein the second uncovered region of the stent is configured to permit tissue ingrowth therein so as to reduce migration of the stent.

Alternatively or additionally to any of the embodiments above, wherein the first covered region is configured to prevent tissue ingrowth along the first covered region of the stent.

Alternatively or additionally to any of the embodiments above, wherein the first covered region, the second uncovered region, or both have a flared end portion.

Alternatively or additionally to any of the embodiments above, wherein a portion of the knitted filament extends through a plurality of interstices defined between adjacent filaments of the one or more interwoven filaments of the first covered region, and wherein the first end of the knitted filament includes a slip knot.

Alternatively or additionally to any of the embodiments above, wherein unraveling the knitted filament causes the slip knot to tighten around the end of the first covered region, and wherein the end of the first covered region collapses radially inward upon tightening of the slip knot.

Alternatively or additionally to any of the embodiments above, wherein the knitted filament includes one or more visual indicia, distance markings, or both.

Another example stent is may comprise a tubular member having a first end and a second end and a lumen extending therein;

a first covered portion disposed along the first end of the tubular member, the first covered portion including one or more interwoven filaments;

a second uncovered portion disposed along the second end of the tubular member; the second uncovered portion adjacent to and attached to the first covered portion;

wherein the first covered portion is configured to prevent tissue ingrowth along the first covered portion;

wherein the second uncovered portion is configured to permit tissue ingrowth therein so as to reduce migration of the stent; and wherein the second uncovered portion includes a knitted filament configured to be unraveled to remove both the first covered portion and the second uncovered portion of the stent while the second uncovered portion remains attached to the first covered portion.

Alternatively or additionally to any of the embodiments above, wherein the one or more interwoven filaments of the first covered portion includes a plurality of braided filaments.

Alternatively or additionally to any of the embodiments above, wherein the one or more interwoven filaments of the first covered portion and the knitted filament of the second uncovered portion form a single knitted filament.

Alternatively or additionally to any of the embodiments above, wherein the knitted filament of the second uncovered portion is attached to the first covered portion at an attachment point.

An example method for removing an implantable medical device may comprise:

engaging a free end of a knitted filament with a removal device, the knitted filament defining a portion of a stent, the stent being positioned within a body lumen;

wherein the stent includes:

a first covered portion;

a second uncovered portion positioned adjacent to and attached to the first covered portion, wherein the second uncovered portion includes the knitted filament;

proximally retracting the free end of the knitted filament to unravel the second uncovered portion while the first covered portion remains attached to the second uncovered portion; and further proximally retracting the unraveled knitted filament to remove the covered portion from the body lumen.

Alternatively or additionally to any of the embodiments above, wherein proximally retracting the free end of the knitted filament to unravel the second uncovered portion while the first covered portion remains attached to the second uncovered portion further includes retracting the removal device through the lumen of the stent and away from the knitted portion such that the stent inverts on itself.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
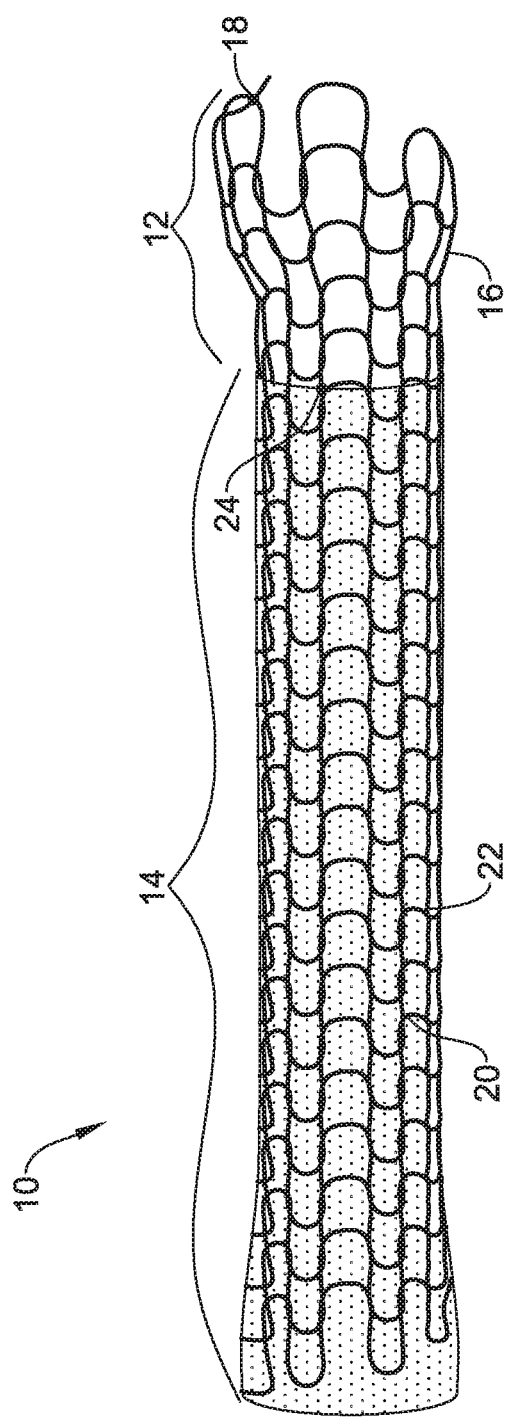
FIG. 1 is a side view of an example implantable medical device.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the disclosure.

FIG. 1 illustrates an example implantable medical device 10. Implantable medical device 10 may be configured to be positioned in a body lumen for a variety of medical applications. For example, implantable medical device 10 may be used to treat a stenosis in a blood vessel, used to maintain a fluid opening or pathway in the vascular, urinary, biliary, tracheobronchial, esophageal, or renal tracts, or position a device such as an artificial valve or filter within a body lumen, in some instances. In some instances, implantable medical device 10 may be a prosthetic graft, a stent-graft, or a stent (e.g., a vascular stent, tracheal stent, bronchial stent, esophageal stent, etc.), an aortic valve, filter, etc. Although illustrated as a stent, implantable medical device 10 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

Over time some implantable stents may become difficult to remove and/or reposition and, therefore, in some instances it may be desirable to remove implantable medical device 10 from a body lumen. In some instances this may be a result of tissue ingrowth through the open, mesh-like configurations (e.g., braids, weaves, knits, etc.) defining the stent geometry. Further, tissue ingrowth may result in a portion of the stent becoming embedded within the tissue of the body lumen. As a result, tearing or similar damage to the vessel wall may occur as the stent is forcibly removed from the body lumen. In order to reduce tissue ingrowth, a covering or sleeve may be disposed over the stent. However, while covering a portion of the stent is effective for reducing tissue ingrowth, the presence of the covering may permit the stent to migrate relative to the implantation target.

Implantable medical device 10 may be designed to include anti-migration characteristics. These design features may permit implantable medical device 10 to be easily removed from a body lumen. For example, implantable medical device 10 may have a first region 14 extending to a first end of the implantable medical device 10 and a second region 12 extending to a second end of the implantable medical device 10. First region 14 and second region 12 may be attached together at a medial location along the length of the implantable medical device 10 to form an expandable tubular framework with open ends and defining a lumen extending therein. First region 14 and/or second region 12 may have a flared end portion, if desired.

In some instances, second section 12 may be defined as an uncovered region (e.g., a tissue ingrowth-promoting section, an anti-migration section, etc.). The uncovered openings present in the second section 12 may permit implantable medical device 10 to be securely implanted (e.g., permit tissue ingrowth) at a target site (e.g., within a body lumen). As will be described in further detail below, second section 12 may be formed of a crocheted wire or filament 16, and thus be described as a knitted section 16.

FIG. 1 further illustrates that first section 14 may define a covered region (e.g., a tissue ingrowth-resistant section, a removable section, etc.) including covering 22 (depicted by the dotted pattern in FIG. 1). First section 14 may include one or more, or a plurality of filaments 20 defining a braid, knit and/or mesh structure. A cover member 22 may be disposed along first section 14 surrounding the braid, knit and/or mesh structure, to thereby extend across openings in the braid, knit and/or mesh structure. Cover member 22 may be designed to reduce tissue ingrowth. Accordingly, cover member 22 may allow first section 14 to be more easily removed from an implantation site at an appropriate time point. Cover member 22 may be formed from a suitable material. For example, cover member 22 may include silicone, polytetrafluoroethylene, polyurethane, or the like, or other materials including those disclosed herein. In some instances, cover member 22 may be disposed along an outer surface of filament(s) 20. In other instances, cover member 22 may be disposed along both an inner and an outer surface of filament(s) 20. In some of these and in other instances, cover member 22 may encapsulate filament(s) 20 or otherwise have filament(s) 20 embedded therein. Coupling cover member 22 to filament(s) 20 may include thermal bonding, molding, coating, dip coating, extruding, adhering, or the like.

Collectively, first and second sections 14/12 may work together to provide a number of desirable characteristics to implantable medical device 10. In some instances, first region 14 may be formed of a knitted wire or filament 20. For example, FIG. 1 shows both first and second region 14/12 including knitted filaments 20/16. In some instances, the knitted filament 20 of covered first section 14 and the knitted filament 16 of second section 12 may define a single continuous knitted filament. In other words, in some instances implantable medical device 10 may include a single, continuous, knitted (e.g., crocheted) filament extending along the entire length of medical device 10 from a first end of medical device 10 (proximate first second 14) to a second end of medical device 10 (proximate second section 12). Further, as shown in FIG. 1, first section 14 may be defined by a portion of the single, continuous knitted filament 20 including a covering 2 disposed thereover.

In other instances, first section 14 and second section 12 may not include a single, continuous knitted filament extending along the entire length of medical device 10. Rather, first section 14 may include a first filament 20 and second section 12 may include a second filament 16 distinct from first filament 20. An end region of first filament 20 may be attached or secured to an end region of second filament 16 adjacent thereto. Thus, first and second sections 14, 12 may include two separate elements which are attached together to form medical device 10.

Figure 2:
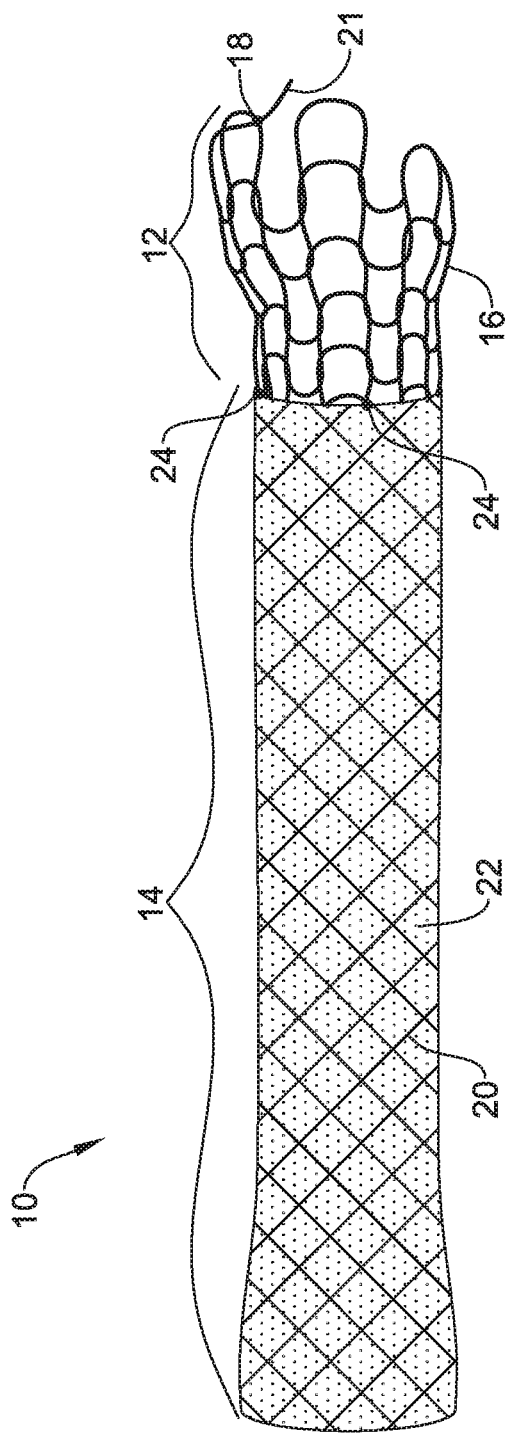
FIG. 2 is a side view of another example implantable medical device.

For example, in some instances first section 14 may be formed of a plurality of braided or interwoven wires or filaments. FIG. 2 illustrates first section 14 including braided or interwoven filaments 20 and second section 12 including knitted filaments 16. In some instances knitted filament 16 of second section 12 may be an extension of, and thus formed unitarily with, one of a plurality of filaments 20 interwoven together through braided first section 14. However, it also contemplated that first section 14 may include one or more knitted or braided filaments 20 defining a separate section that is attached to knitted filament 16 of second section 12. In other words, first section 14 may be defined as a component (distinct from section 12) including one or more, or a plurality of braided and/or knitted filaments 20 which are attached (e.g., welded, interwoven, etc.) to the knitted filament 16 of second section 12.

FIG. 2 further shows first section 14 attached second section 12 via one or more attachment points 24. Additionally, FIG. 2 shows the free end 21 of the filament 16 being attached to another location along filament 16 via an attachment point 18. It can be appreciated that the free end 21 of filament 16 may need to be attached to another location along filament 16 to prevent inadvertent unraveling of second section 12.

Figure 3:
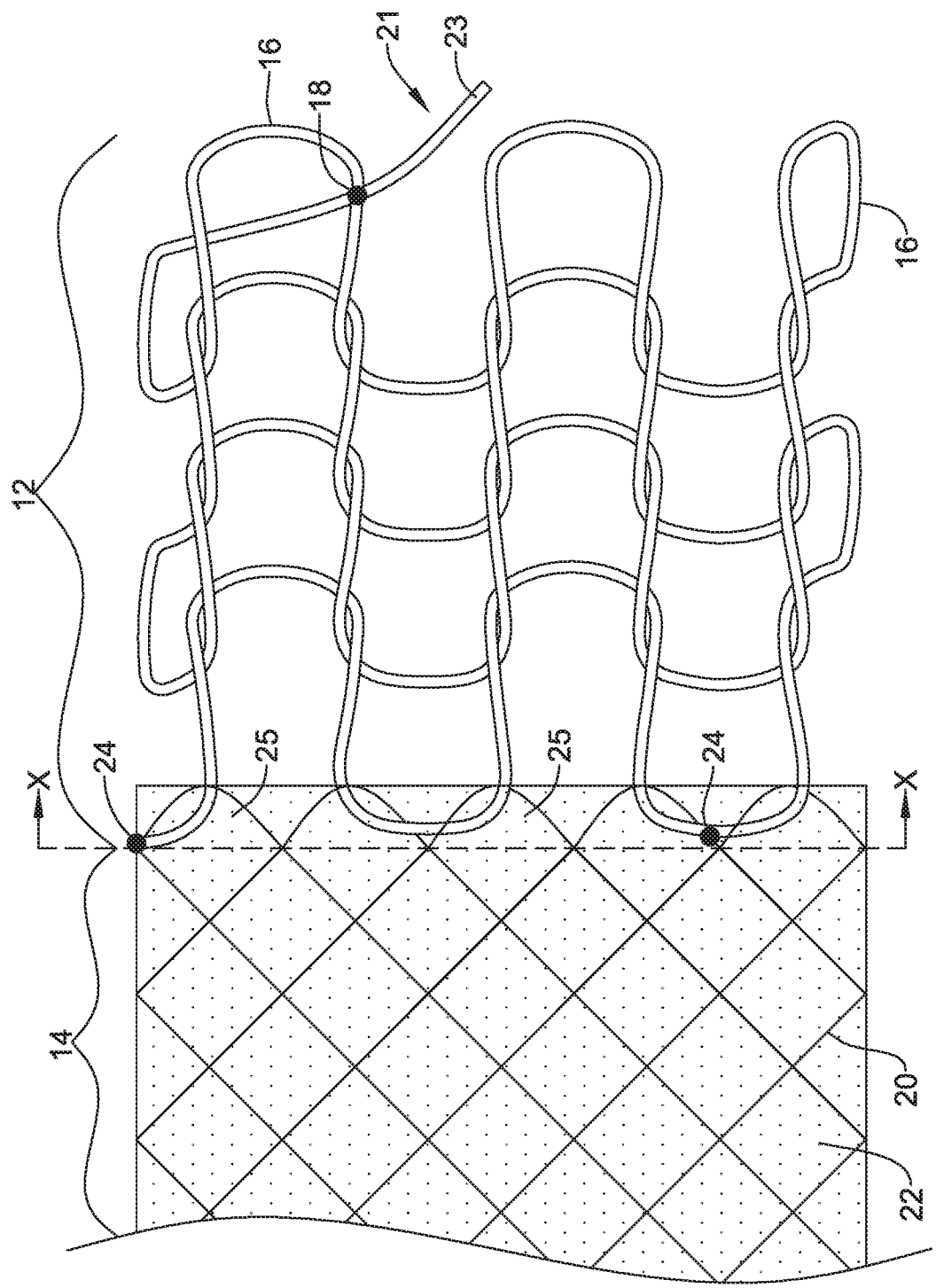
FIG. 3 illustrates a portion of an example implantable medical device.

FIG. 3 shows a close-up view of second section 12 and a portion of first section 14. In some examples, second section 12 may be formed by knitting or crocheting filament 16 into a desired configuration. The knitted or crocheted configuration of filament 16 may take the form of a series of loosely associated loops that are interconnected in a manner that allows filament 16 to maintain its integrity while in a cylindrical configuration, while also allowing for relatively easy unraveling by, for example, simply proximally pulling on release member 23 (e.g., the end of filament 16 itself or a tab attached to the end of filament 16)). In other words, the configuration of the loops of the knitted or crocheted filament 16 allows for filament 16 to be pulled (e.g., by grasping and pulling release member 23) and unraveled. In addition, the looped framework of knitted or crocheted filament 16 may also define a series of openings that allow for tissue disposed along the surface of second section 12 to engage and grow within the openings. This may allow second section 12 to become secured with surrounding tissue in a manner that reduces the ability of implantable medical device 10 to migrate within a target body lumen.

As shown in FIG. 3 and described above, second section 12 may be defined by a single filament 16. Single filament 16 may be knitted in a manner which permits it to unravel into a single, continuous filament. For example, filament 16 may be configured as a knitted, generally cylindrical matrix that, upon the appropriate actuation, can be unraveled from a first configuration (e.g., cylindrical) to a second unraveled configuration (e.g., into a substantially "linear" configuration). While FIG. 3 depicts filament 16 knitted in a particular pattern, it can be appreciated that a variety of patterns, loops, designs, weaves, etc. may be utilized to construct knitted section 12 having the properties (e.g., ability to unravel) as described herein. Filament 16 may be a solid member of a round or non-round cross-section or may be tubular (e.g., with a round or non-round cross-sectional outer surface and/or round or non-round cross-sectional inner surface).

As stated above, in some examples first section 14 may be attached to second section 12 via one or more attachment points 24 at a junction between first section 14 and second section 12 in a medial region of the implantable medical device 10. In some instances, attachment point 24 may be defined as a weld point. For example, in some instances a portion of filament 16 defining second section 12 may be welded onto a portion of filament(s) 20 defining first section 14. Additionally, FIG. 3 shows filament 16 interlaced (e.g., interwoven) through one or more interstitial apertures (e.g., loop portions) 25 formed from one or more of the filaments 20 forming an end portion of first section 14. In other words the end of first section 14 at the junction with second section 12 may include a plurality of closed loops formed by the one or more filaments 20, wherein filament 16 may be interlaced through the closed loops.

It can be appreciated that one or more of attachment points 24 may define a structure that is capable of terminating further unraveling of filament 16 of second section 12 beyond attachment point 24 (e.g., beyond the junction between first section 143 and second section 12). For example, one or more of attachment points 24 may be designed in a manner that effectively stops filament 16 from unraveling and/or further separating from filament 20 of first section 14. For instance, when filament 16 and filament 20 are a single continuous filament, the attachment point 24 may prevent further unraveling of the filament beyond attachment point 24 after the second section 12 has been unraveled such that the knitted/braided configuration of the covered second section 14 remains in its tubular configuration. It is noted that in such a configuration, the second section 14 may be a knitted section formed from the single continuous filament 16/20 or the second section 14 may be a braided section formed by interweaving or braiding the single continuous filament 16/20 with one or more additional filaments. It can further be appreciated that attachment point 24 may be designed to have sufficient strength such that it overcomes a removal force imparted thereon.

As stated above, FIG. 3 also shows an additional attachment point 18. As described above, attachment point 18 may define a portion of second section 12 in which the free end 21 of filament 16 is attached onto itself, thereby preventing filament 16 from inadvertently unraveling. Attachment point 18 may be configured to break away and thereby release the free end of filament 16 from the remainder of uncovered knitted section 12. In other words, by applying a force (e.g., manual torqueing), the attachment point (e.g., the weld) may be broken, thereby separating the free end of filament 16 from the remainder of uncovered knitted section 12.

FIG. 3 also illustrates release member 23, which may be an end region of filament 16 or another structure secured to end region of filament 16. In at least some instances, release member 23 may take the form of an enlarged, graspable region at the end of filament 16. The precise form of release member 23 may vary. For example, release member 23 may be a tab, loop, enlarged section, flattened section, droplet of a polymer or adhesive, etc. Release member 23 may be a portion of filament 16 that can be relatively easily grasped and pulled (e.g., by a removal device) in order to unravel filament 16. Release member 23 may be disposed along second section 12 and may be utilized to partially collapse and/or otherwise aid in removal of second section 12.

In some instances, release member 23 may be generally designed so that pulling (e.g., proximally pulling) on release member 23, and thereby putting filament 16 in tension, may exert a radially inward force onto the end region of first section 14, effectively shifting the end portion of first section 14 to a more conical or partially collapsed configuration, which may make it easier to remove implantable medical device 10 (e.g., first section 14).

Figure 4:
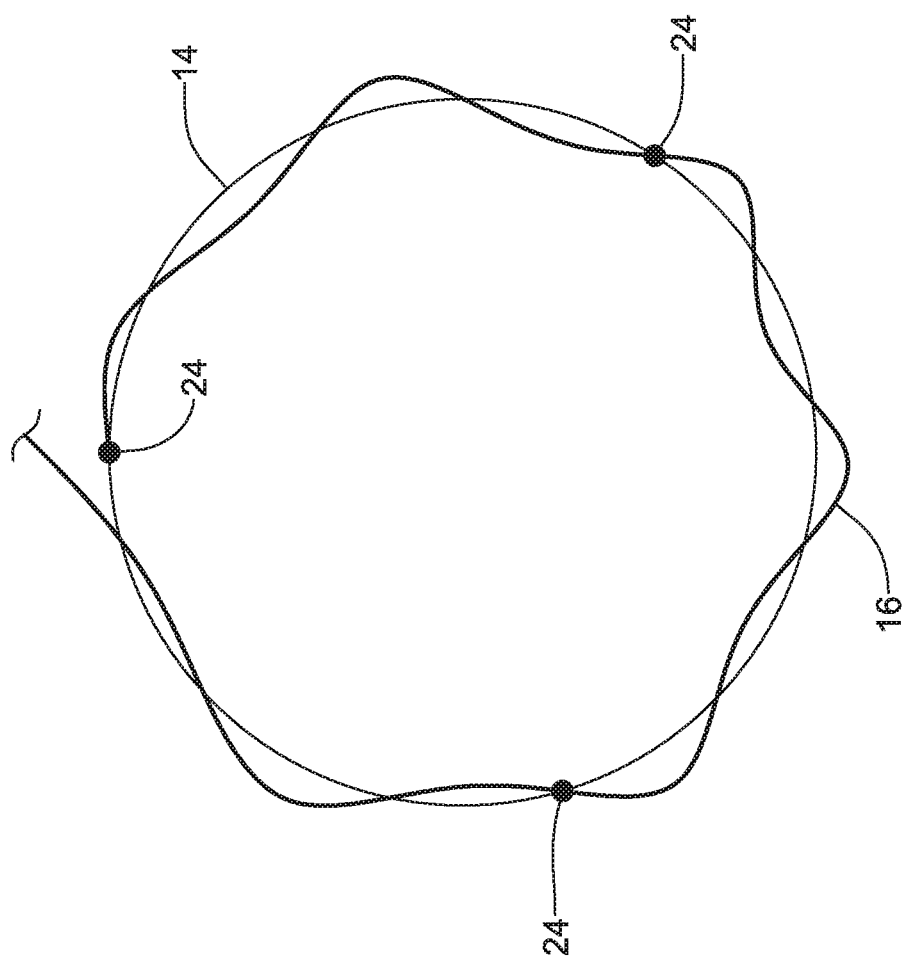
FIG. 4 illustrates a cross-section of an example implantable medical device.

FIG. 4 shows a cross-sectional view along line X-X of FIG. 3. As shown in FIG. 4 and described above, filament 16 may be interlaced through the closed loops or openings (e.g., interstitial loops) 25 formed from the end portion of section 14. As shown, filament 16 may interweave through one or more of the interstitial openings as it travels around the circumference of section 14. Additionally, FIG. 4 shows the one or more attachment points 24 disposed along the circumference of stent portion 14. While FIG. 4 shows three attachment points 24 positioned substantially equidistant apart from one another, it is contemplated that less than or greater than three attachment points may be utilized to attach stent section 14 to stent section 12. For example, 1, 2, 3, 4, 5, 6, 7, 8, 9, 10, 15, 20, or more attachment points 24 may be utilized. Further, attachment points 24 may be offset from one another in any formation desired. In some instances, cover member 22 may extend over and/or surround closed loops or openings 25 and/or attachment points 24, preventing tissue ingrowth.

One or both of sections 12/14 may be designed to shift between a first or "unexpanded" configuration and a second or "expanded" configuration. In at least some instances, one or both of sections 12/14 are formed from a shape memory material (e.g., a nickel-titanium alloy such as nitinol) that can be constrained in the unexpanded configuration, such as within a delivery sheath, during delivery and that self-expands to the expanded configuration when unconstrained, such as when deployed from a delivery sheath and/or when exposed to a pre-determined temperature conditions to facilitate expansion. In other instances, one or both of sections 12/14 may be designed to be actively expanded by a suitable expansion member or device such as, for example, a balloon. The precise material composition of sections 12/14 can vary, as desired, and may include the materials disclosed herein.

Figure 5:
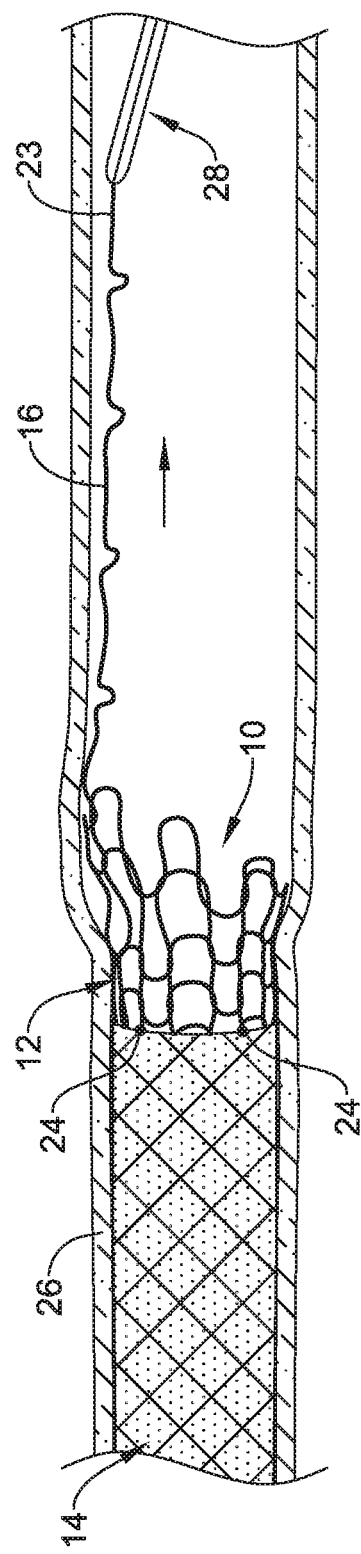
FIGS. 5 and 6 illustrate an example implantable medical device being removed from a body lumen.

FIG. 5 illustrates a portion of implantable medical device 10 implanted along a body lumen 26. As discussed herein, while implantable medical device 10 is implanted along body lumen 26, tissue ingrowth may occur along first section 12, which may reduce migration of implantable medical device 10 within body lumen 26, while tissue ingrowth may be prevented along second section 14.

However, in some examples, it may be necessary to remove implantable medical device 10 from body lumen 26. FIG. 5 illustrates a portion of a process for removing implantable medical device 10 from example body lumen 26. As shown in FIG. 5, a removal device 28 may be used to grasp release member 23 and break attachment point 14. After grasping release member 23, removal device 28 may be proximally retracted until second section 12 unravels and is pulled into an unraveled "linear" configuration shown in FIG. 6. In instances where tissue ingrowth has occurred along second section 12, unraveling filament 16 may occur in a manner that allows filament 16 to be pulled from the ingrown tissue (e.g., in a manner similar to pulling a suture from a closed wound).

Figure 6:
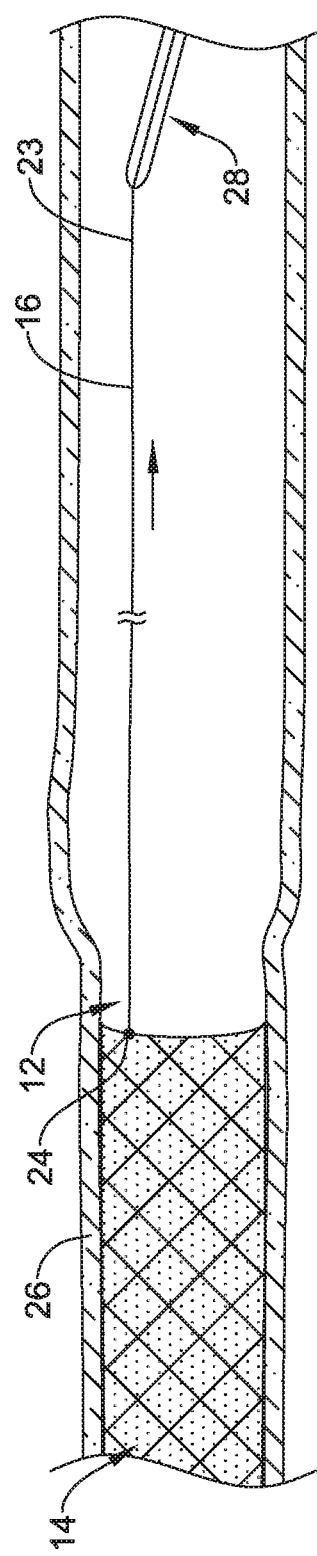

After filament 16 is unraveled into the linear configuration shown in FIG. 6, it may continue to be pulled proximally in order to remove first section 14 from the body lumen 26. In other words, removing first section 14 may include simply pulling second section 14 via filament 16 (with filament 16 attached to second section 14) from the body lumen 26 (and, ultimately, the patient).

Figure 7:
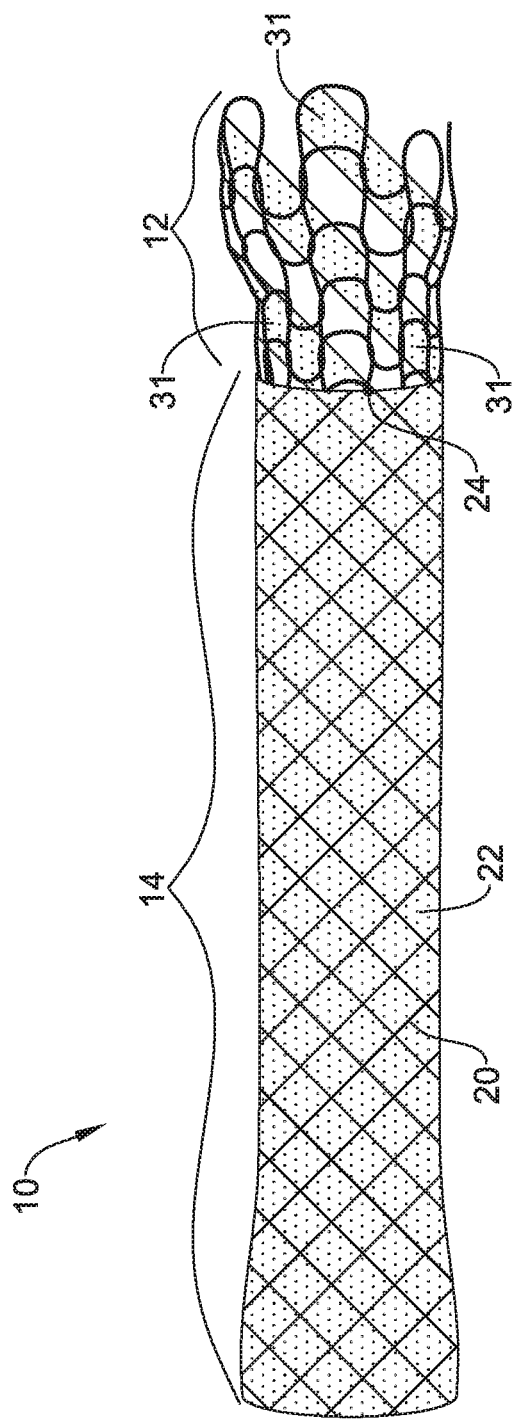
FIG. 7 illustrates another example implantable medical device.

FIG. 7 shows another embodiment of medical device 10. The device shown in FIG. 7 depicts one or more covering strips or stripes 31 disposed on second section 12. As shown in FIG. 7, the covering stripes 31 may extend around second section 12 in a general helical pattern, substantially extending around the circumference of second section 12. The covering stripes 31 may also extend along the entire longitudinal length of second section 12. It should be understood that pattern of covering 22 shown in FIG. 7 is merely one of many patterns of covering 22 that may be applied to second section 12.

The covering stripes 31 shown in FIG. 7 may be formed from the same or a similar covering 22 described above with respect to first section 14. As discussed above with respect to first section 14, covering stripes 31 may be utilized to inhibit, reduce or prevent a portion of second section 12 from becoming embedded into tissue positioned adjacent the covering 22. In some instances, covering stripes 31 may be oriented on second section 12 to cover 10% to 90%, 20% to 80%, 30% to 70%, or 40% to 60%, of a surface area around the circumference of second section 12. In some instances, covering stripes 31 may be arranged such that an imaginary line extending parallel to the central longitudinal axis of the device 10 at any circumferential location around the circumference of second section 12 will intersect one or more of the covering stripes 31.

Figure 8:
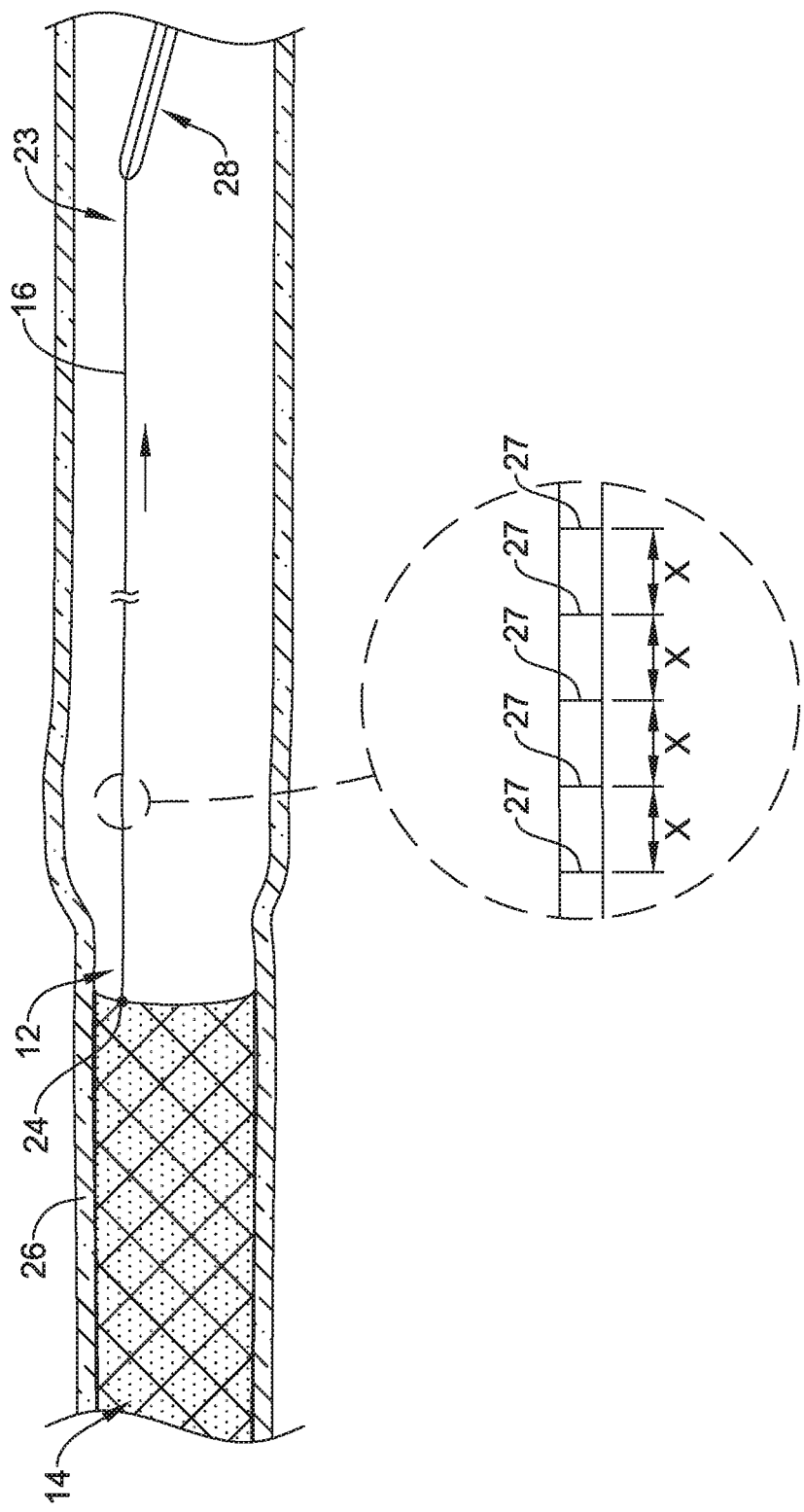
FIG. 8 illustrates another example implantable medical device.

FIG. 8 shows another example medical device 10 having filament 16 pulled to a linear configuration as described above with respect to FIG. 6. Further, the detailed view of FIG. 8 shows that in some examples, filament 16 may include visual indicia and/or graduated markings 27 spaced along the length of filament 16. As shown in FIG. 8, the distance between markings 27 is depicted as "X." In some instances the distance (e.g., spacing) "X" between markings 27 may be equal. In other words, in some examples markings 27 may be equidistant from one another. However, in other instances markings 27 may be spaced apart from one another at different distances. It can be appreciated that markings 27 may provide a clinician with information regarding how much of filament 16 remains in the body, how much of second section 12 has been unraveled and/or how much of second section remains to be unraveled as the clinician withdraws a portion of filament 16 from the patient. Additionally, markings 27 may provide a clinician with the ability to measure how quickly medical device 10 is being removed from a patient. For example, when removing the filament through the mouth (or other body opening) of a patient, the clinician may visually observe the markings 27 on filament 16 as filament 16 exits the mouth (or other body opening) of the patient.

Figure 9:
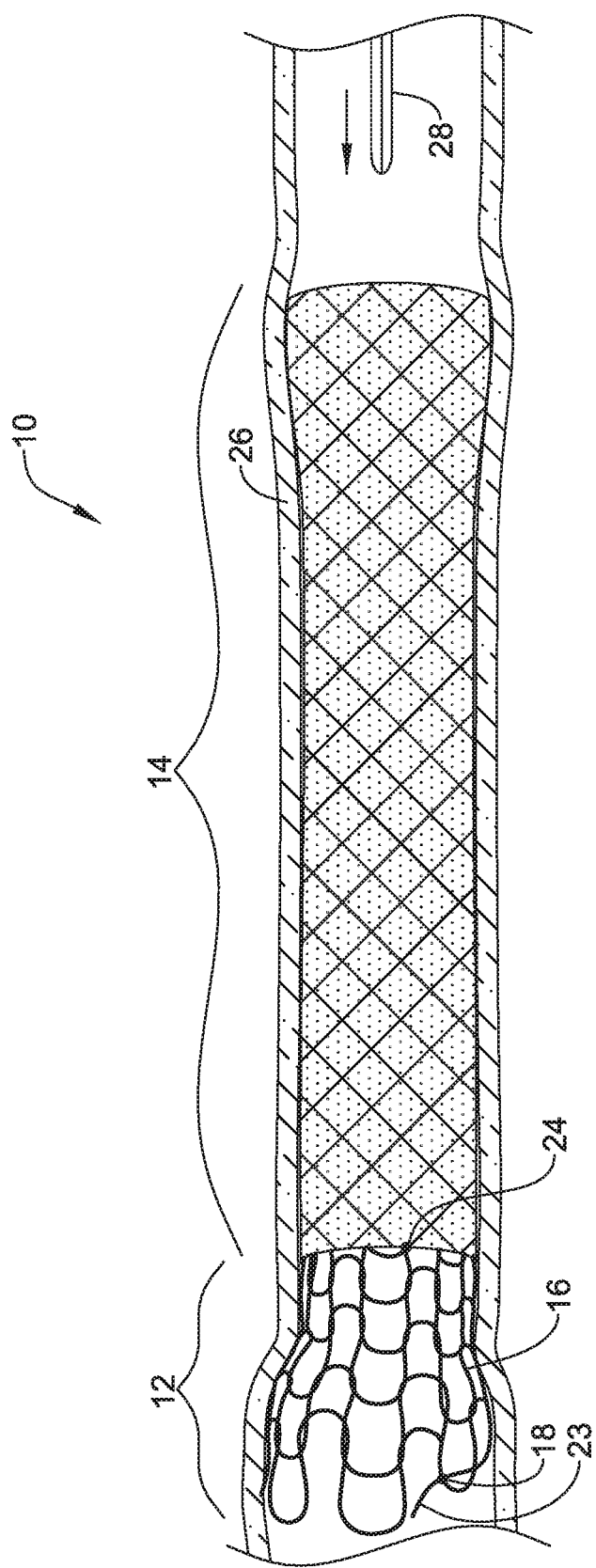
FIGS. 9-11 illustrate another example implantable medical device being removed from a body lumen.
Figure 10:
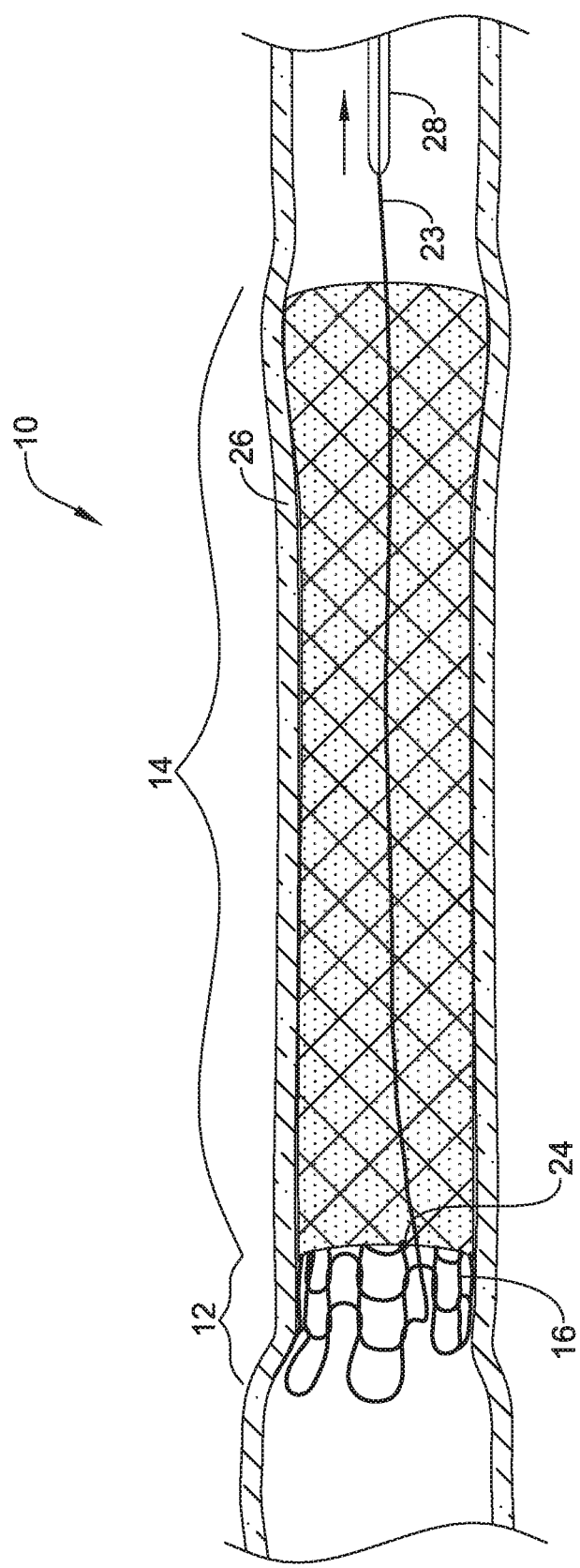
Figure 11:
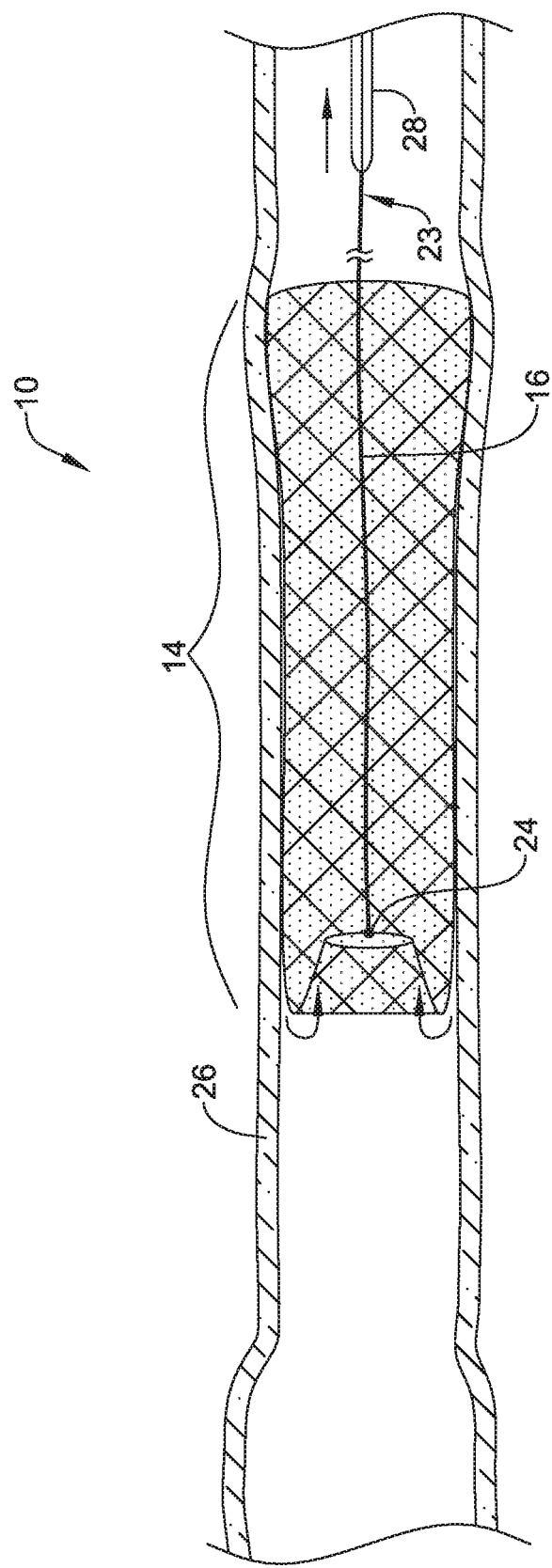

FIGS. 9-11 depict an alternative methodology for removing an implanted medical device 10 from a body lumen 26. In the example shown in FIG. 9, medical device 10 has been positioned in a body lumen (e.g., the esophagus) such that uncovered second section 12 is oriented distally of first section 14, e.g., uncovered second section 12 is pointed toward the stomach and first section 14 is pointed toward the mouth of a patient. As can be appreciated from FIG. 9, because release member 23 is positioned away from the mouth of the patient, removal device 28 may need to be advanced through the lumen of medical device 10 (e.g., through the lumen of first section 14 and the lumen of second section 12) in order for removal device 28 to grasp release member 23 and initiate the unraveling of second section 12.

Having grasped release member 23, removal device 28 may be withdrawn back through the lumen(s) of second and first sections 12/14. Similar to that described above with respect to FIGS. 5 and 6, filament 16 of second section 12 may unravel until the unraveling terminates at attachment point 24.

Once unraveled, further retraction of removal member 28 may cause the portion of first section 14 to "invert" on itself. For example, the arrows shown in FIG. 11 depict how the end portion of first section 14 may invert toward a central longitudinal axis of first section 14. Further, as removal device 28 continues to be retracted toward the mouth of the patient, first section 14 may continue to "roll" upon itself for its entire length, inverting into and through the lumen of first section 14. In other words, first section 14 may roll away from body lumen 26 into the lumen of a more proximal portion of first section 14 as removal device 28 is retracted out of the patient's body. As the first section 14 is inverted, the radially outward surface of first section 14 is turned inward to become the radially inward surface while the radially inward surface of first section 14 become the radially outward surface once fully inverted. Accordingly, this removal process may avoid the radially outward surface of first section 14 from sliding across the luminal surface of the body lumen 26 as the first section 14 is withdrawn proximally. For example, in instances in which the first section 14 of medical device 10 is positioned across a tumor, inverting the first section 14 during removal may avoid sliding first section 14 across the tumor and/or otherwise irritating the section of the body lumen 26 in which the medical device was positioned. It can be appreciated that this method of removing medical device 10 is different than that described with respect to FIGS. 5 and 6. Specifically, in FIGS. 5 and 6, medical device 10 may be pulled, and therefore, slide along body lumen 26 as it is pulled via filament 16. This method of removal is different than the inverted rolling methodology depicted in FIGS. 9-11.

Figure 12:
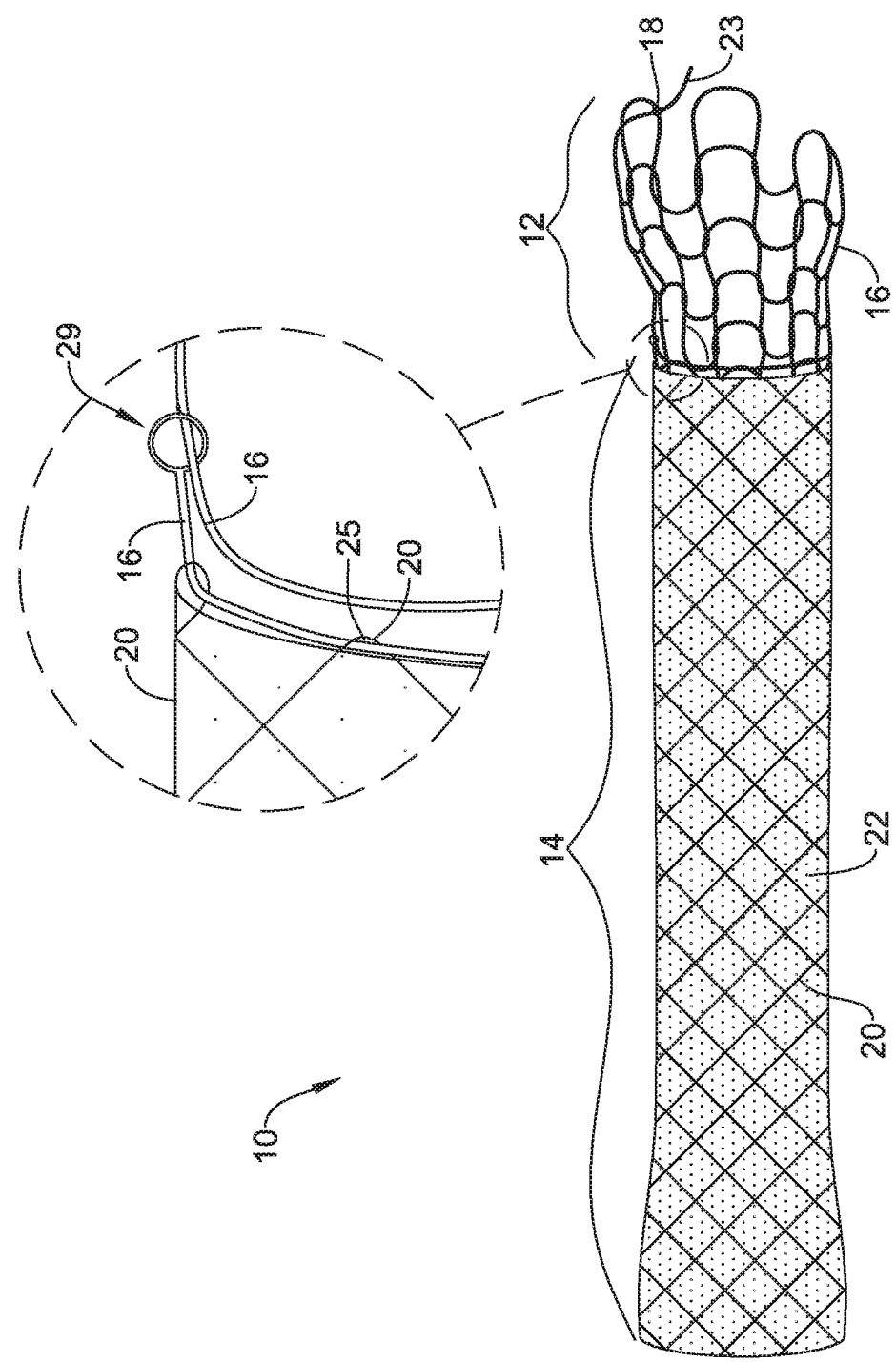
FIG. 12 illustrates another example implantable medical device.
Figure 13:
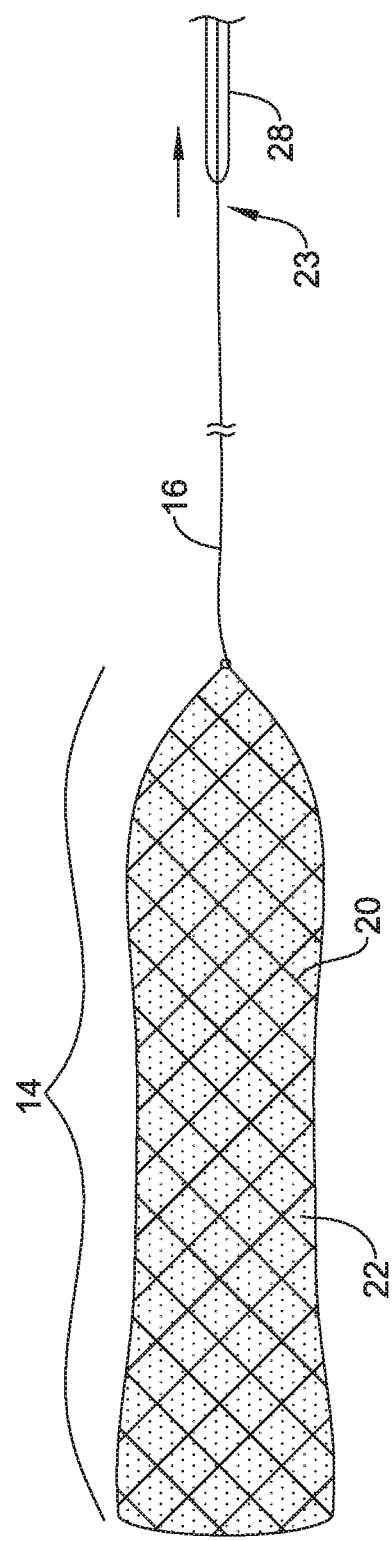
FIG. 13 illustrates another example implantable medical device being removed from a body lumen.

FIGS. 12 and 13 illustrate an additional example medical device 10. As shown in the detailed view of FIG. 12 and similar to the that described above, filament 16 of second section 12 may be attached to the interstitial loops 25 formed from filaments 20 of the end portion of first section 14 at the junction between first section 14 and second section 12. In other words, filament 16 may be interlaced among one or more interstitial loops 25 of first section 14. Additionally, FIG. 12 shows an end of filament 16 including a loop or slip knot 29. In some examples intermediate portion of filament 16 may be threaded through loop slip knot 29.

FIG. 13 illustrates the proximal retraction of removal device 28. As can be appreciated from FIG. 13, the proximal retraction of removal device 28 may cause the end of first section 14 to radially compress on itself. In other words, as filament 16 is pulled through loop or slip knot 29, the looped portion of filament 16 may cinch down causing the loop portions 25 of first section 14 to tighten radially inward toward the central longitudinal axis of first section 14. The tightening of the end portion of first section 14 may result in a narrowed end portion (as shown in FIG. 13). This narrowed end portion be provide a desirable geometry to remove medical device 10 from body lumen 26.

It is further contemplated that any of the examples described herein may include a radiopaque marker designed to provide position and/or visual confirmation of the location of one or more structural features of medical device 10. For example, it is contemplated that radiopaque markings may be placed on one or more of the attachment points 18/24 and/or release member 23 to aid engagement and unravelling of the uncovered anti-migration section 12.

The materials that can be used for the various components of implantable medical device 10 (and/or other devices disclosed herein) and the various tubular members disclosed herein may include those associated with medical devices. Implantable medical device 10, and/or the components thereof, may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of device 10 to achieve the same result.

In some embodiments, a degree of Magnetic Resonance Imaging (MRI) compatibility is imparted into device 10. For example, device 10, or portions thereof, may be made of a material that does not substantially distort the image and create substantial artifacts (e.g., gaps in the image). Certain ferromagnetic materials, for example, may not be suitable because they may create artifacts in an MRI image. Device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments.

What is claimed is:

1. A stent comprising:
    a first covered region formed of one or more interwoven filaments and a covering; and
    a second uncovered region adjacent the first covered region, wherein the second uncovered region includes a knitted filament;
    wherein a first end of the knitted filament is attached to the first covered region;
    wherein a second end of the second uncovered region, opposite the first end, includes a free end of the knitted filament;
    wherein pulling the free end results in unraveling of the knitted filament to remove both the first covered region and the second uncovered region of the stent while the first end of the knitted stent remains attached to the first covered region.

2. The stent of claim 1, wherein the one or more interwoven filaments of the first covered region include a plurality of braided filaments.

3. The stent of claim 1, wherein the one or more interwoven filaments of the first covered region include a knitted filament.

4. The stent of claim 3, wherein the knitted filament of the second uncovered region and the knitted filament of the first covered region comprise a single knitted filament.

5. The stent of claim 1, wherein the first end of the knitted filament is attached to the first covered region at a first attachment point.

6. The stent of claim 5, wherein the first attachment point is a weld configured to terminate the unraveling of the knitted filament beyond the first attachment point.

7. The stent of claim 1, wherein the knitted filament of the second region includes a second end, and wherein the second end is attached to an intermediate portion of the knitted filament at a second attachment point.

8. The stent of claim 7, wherein the second attachment point is a weld configured to separate from the intermediate portion of the knitted filament.

9. The stent of claim 1, wherein the second uncovered region of the stent is configured to permit tissue ingrowth therein so as to reduce migration of the stent.

10. The stent of claim 1, wherein the first covered region is configured to prevent tissue ingrowth along the first covered region of the stent.

11. The stent of claim 1, wherein the first covered region, the second uncovered region, or both have a flared end portion.

12. The stent of claim 1, wherein a portion of the knitted filament extends through a plurality of interstices defined between adjacent filaments of the one or more interwoven filaments of the first covered region, and wherein the first end of the knitted filament includes a slip knot.

13. The stent of claim 12, wherein unraveling the knitted filament causes the slip knot to tighten around the end of the first covered region, and wherein the end of the first covered region collapses radially inward upon tightening of the slip knot.

14. A stent comprising:
a first covered region formed of one or more interwoven filaments and a covering; and
a second uncovered region adjacent the first covered region, wherein the second uncovered region includes a knitted filament;
wherein a first end of the knitted filament is attached to the first covered region;
wherein the knitted filament is configured to be unraveled to remove both the first covered region and the second uncovered region of the stent while the first end of the knitted stent remains attached to the first covered region;
wherein the knitted filament of the second region includes a second end, and wherein the second end is attached to an intermediate portion of the knitted filament at a second attachment point;
wherein the second attachment point is configured to separate from the intermediate portion of the knitted filament;
wherein separating the attachment point from the intermediate portion of the knitted filament permits the unraveling of the second uncovered region of the stent.

15. A stent, comprising:
a tubular member having a first end and a second end and a lumen extending therein;
a first covered portion disposed along the first end of the tubular member, the first covered portion including one or more interwoven filaments forming a tubular structure;
a second uncovered portion disposed along the second end of the tubular member; the second uncovered portion adjacent to and attached to the first covered portion;
wherein the first covered portion is configured to prevent tissue ingrowth along the first covered portion;
wherein the second uncovered portion is configured to permit tissue ingrowth therein so as to reduce migration of the stent;
wherein the second uncovered portion includes a knitted filament configured to be unraveled to remove both the first covered portion and the second uncovered portion of the stent while the knitted filament of the second uncovered portion remains attached to the tubular structure of the first covered portion; and
wherein the knitted filament of the second uncovered portion is attached to the first covered portion at an attachment point configured to terminate the unraveling of the knitted filament beyond the attachment point.

16. The stent of claim 15, wherein the one or more interwoven filaments of the first covered portion includes a plurality of braided filaments.

17. The stent of claim 15, wherein the one or more interwoven filaments of the first covered portion and the knitted filament of the second uncovered portion form a single knitted filament.

18. The stent of claim 15, wherein the second uncovered portion includes a single knitted filament that is distinct from any of the one or more interwoven filaments of the first covered portion.

* * * * *